United States Patent [19]

Hornlein et al.

[11] Patent Number: 4,846,790
[45] Date of Patent: Jul. 11, 1989

[54] ULTRASONIC SURGICAL SYSTEM WITH IRRIGATION MANIFOLD

[75] Inventors: Robert W. Hornlein, Stamford; Joseph N. Logan, Trumbull, both of Conn.; Alan Broadwin, Brooklyn, N.Y.; Vaclav O. Podany, New Fairfield, Conn.

[73] Assignee: Cooper LaserSonics, Inc., Santa Clara, Calif.

[21] Appl. No.: 198,835

[22] Filed: May 26, 1988

Related U.S. Application Data

[62] Division of Ser. No. 849,830, Apr. 9, 1986, Pat. No. 4,747,820.

[51] Int. Cl.⁴ ............................................. A61B 17/32
[52] U.S. Cl. ...................................... 604/22; 604/43; 128/24 A
[58] Field of Search .................. 604/22, 35, 39, 40, 604/43, 198, 283; 128/24 A, 303

[56] References Cited

U.S. PATENT DOCUMENTS

| | | | |
|---|---|---|---|
| 3,589,363 | 6/1971 | Banko | 604/22 |
| 4,063,557 | 12/1977 | Wuchinich et al. | 604/22 |
| 4,223,676 | 9/1980 | Wuchinich et al. | 604/22 |
| 4,246,902 | 1/1981 | Martinez | 604/22 |
| 4,508,532 | 4/1985 | Drews et al. | 604/22 |
| 4,515,583 | 5/1985 | Sorich | 604/22 |

Primary Examiner—Stephen C. Pellegrino
Attorney, Agent, or Firm—Vorys, Sater, Seymour & Pease

[57] ABSTRACT

An ultrasonic surgical aspirator having an improved irrigation/aspiration manifold and components to facilitate quick connections of the irrigation and aspiration lines to a handpiece. In combination with a handle assembly having an ultrasonic vibrator for vibrating an ultrasonic tip and a nosecone, a nosecone extension defining a rotating joint for connection to the nosecone in an articulating joint for connection to a rigid or flexible flue is provided. The nosecone extension further defines an irrigation cowl having an irrigation port for receiving an irrigation connector for connecting the irrigation fluid to the nosecone extension for passage of irrigation fluid through the nosecone extension and a flue about the surgical tip. An aspiration tubulation connector adapted to securely fit a slot through the nosecone and nosecone extension connects an aspiration port on the tip to the aspiration tube for connection to a pump into a discard area. An alternative manifold assembly includes a nosecone extension adapter defining a rotating joint for connection to the nosecone in a cylindrical portion for connection to an extender sheath, the opposite end of which is connected to a flue adapter defining an articulating joint for connection to a flue. Such an alternative manifold assembly is particularly adapted for use in elongated and curved tips with extenders. The detailed structure of the aspiration tubular connector and the irrigation connector is also shown.

7 Claims, 9 Drawing Sheets

ULTRASONIC SURGICAL SYSTEM WITH IRRIGATION MANIFOLD

BACKGROUND OF THE INVENTION

This is a divisional of application Ser. No. 849,830 filed on Apr. 9, 1986, now U.S. Pat. No. 4,747,820.

This invention relates to an ultrasonic surgical aspiration system. More particularly, this invention relates to an impoved irrigation/aspiration manifold and associated parts for such an ultrasonic surgical aspiration system. Still more particularly, this invention relates to the use of mating connections in such a system to allow easy, rapid, and foolproof connections to the irrigation, aspiration, and tissue relief ports in an ultrasonic surgical aspiration system. In addition, this invention relates to an improved transition member which allows an easy exchange of flues, articulation without leakage, and a swivel joint which permits use of curved ultrasonic members in an ultrasonic surgical aspiration system.

Ultrasonic surgical devices are known for performing a number of surgical procedures. A representative device is shown in U.S. Pat. No. 3,589,363 describing a hand-held instrument having an operative tip vibrating at a frequency in the ultrasonic range, and in which a handpiece includes a transducer. Connections are provided on the handpiece to a source of treatment fluid and to a pump to withdraw suspended tissue particles in a fluid from an operative site.

The design of such ultrasonic surgical devices has depended not only on the technical and functional requirements of a resonant body, but also upon their surgical application. Thus, the parameters of the system, the length of the tip, and the tip stroke and diameter to be acceptable for a useful surgical device in various operative site areas have developed over the years, based upon experience with such devices. Attention has been paid in the art to the development of the various components in the system, with the result that an ultrasonic surgical aspiration instrument is well-known and used as a sophisticated hightechnology surgical instrument.

Such a system has been developed and produced by the assignee of this invention which comprises an assembly of an acoustic vibrator, a nosecone, a flue, a handpiece and a manifold. The assembled system provides a source of irrigation fluid to an operative site and the aspiration of surgically-excised particles from the site under the control of precise and sophisticated instrumentation. A number of modifications to such a basic system have been made with respect to such items as the length and shape of the tip, its coupling with a transducer, the use of an extender (whether curved or straight), and others. Usually, the components for a surgical use are provided as a part of a sterile surgical kit to be used and discarded after each surgical procedure.

The acoustic vibrator assembly includes the combination of a transducer connected to a handpiece for providing a source of ultrasonic vibrations to a tip. When the tip is connected to the transducer, or to a straight or curved extender interposed between the tip and the transducer, provisions are made in the kit for connecting the components to a predetermined level of tightness. A nosecone assembly is then assembled from a nosecone which is provided with O-ring seals in grooves in the nosecone and slid over the accoustic vibrator until seated. A flue is slid over the tip and hand tightened to the nosecone to provide a passage within the flue and about the length of the tip for irrigation fluid from the nosecone to the tip. A nosecone adapter may be used with an extender flue to provide alternative length and shapes for the convenience of the surgeon and safety for the patient for particular operations. When used, the nosecone adapter is tightened to the nosecone and the extender flue is gently pushed over the tip of the nosecone so that the curve of the extender and flue match without the flue touching the tip. The body of the flue adapter is twisted to centralize the tip within the flue. Thereafter, the acoustic vibrator and the nosecone with the flue attached are inserted into a handpiece housing and seated so that the fluid manifold assembly may be completed.

An irrigation tube with a flexible applicatior cable is fed through a slot in the nosecone and through an aspiration port on the exterior of the tip. By gently pulling the cable through the port in the tip, the aspiration tubing attaches to the aspiration port on the tip. The other end of the aspiration tubing is connected about a pump to control aspiration pressures and to a discard region for discarding extracted tissue. Metallic clips are provided to secure the aspiration tubing to the exterior of the handpiece housing. Thereafter, irrigation tubing is connected to the irrigation port on the nosecone for connection at its other end to a source of irrigation fluid, such as an IV bottle. Additional clips are provided to the handpiece cable to secure the manifold.

Thus, the assembled system is able to provide irrigation fluid from an irrigation fluid source through tubing to an irrigation port and through the nosecone into the area intermediate the tip and the flue to irrigate the surgical site adjacent the tip extending from the flue. Aspiration occurs from the operative site through an aspiration passage to the aspiration port and through the aspiration tubing to aspirate surgically-excised particles.

As can be seen from the above simplified descritption, several fluid connections must be made at the surgical handpiece and elsewhere to provide irrigation to and aspiration from the surgical site. While such prior designs were satisfactory, they utilized plain tubing ends which require skilled and special application techniques for making the connections. In addition, the assembly procedure was further complicated by the number of tips and extended options available to the surgeon. It thus remained a problem in the art to assure easy, rapid and foolproof connection of the irrigation, aspiration and tissue release ports to the correct tubing and location, since such connections are made in an operating room in preparation for surgery or during the surgical procedure itself in certain situations where modification or reconnection is needed.

Thus, it is a main objective of this invention to provide a mating component system for an ultrasonic surgical vibrator which uses quick-connecting devices to facilitate connection of the components and tubing to the irrigation, aspiration and tissue release ports.

It is another object of this invention to provide an improved transition piece to permit an easy exchange of flues between a rigid flue and a ribbed flexible flue for easy connection to an assembly of a handle, nosecone, and tip.

It is an additional object of this invention to provide a nosecone extension which provides a rotating joint for assembly to a nosecone and an articulating joint for connection to either a rigid flue secured with or without O-ring or to a ribbed flexible flue.

It is a further object of this invention to provide a ribbed flexible flue structure for convenient use with an ultrasonic surgical aspiration system of the type described.

It is a further object of this invention to provide a nosecone extension adapter for ready connection to an extender connected to an assembly of a handle, nosecone, and vibrator for receiving therein an extended tip and an extender sheath which is connected to the nosecone extension adapter for connection between the extender sheath and a flue adapter having an articulating joint for receiving either a ribbed flexible flue or a rigid flue as described.

It is an additional object of this invention to provide an aspiration tubulation connector for secure connection to an aspiration tube and quick, secure connection with limited motion to the aspiration port on the tip within a confined space in the interior of the handpiece.

It is a further object of this invention to provide a quick connect fitting for connection between an end of the irrigation tube and the irrigation tube fitting by turning and locking, and easy connection to an irrigation port on a transition member or nosecone extender.

It is a more general object of this invention to provide an ultrasonic surgical aspiration system with conveniently-usable components capable of easy assembly in diverse combinations while minimizing error in the assembly, which components are adapted for easy fluid connection.

These and other objects of the invention will become apparent from the written description of the invention which follows.

BRIEF SUMMARY OF THE INVENTION

Directed to achieving the foregoing objects and to overcoming problems in the art, in one aspect, the invention relates to a nosecone extension member defining at its inlet end a rotating joint for secure connection to a nosecone in an ultrasonic surgical system, and an articulating joint at its outlet end for connection to either an articulated rigid flue having an O-ring seal to prevent leakage, or to a ribbed flexible flue for use with curved tip members. The rigid flue is preferably optically transparent, having a tapered body defined in cross-section by an annular wall terminating at its connecting end in an arcuate seal portion to receive therein an O-ring for connection to the articulating joint on the nosecone extension or on a flue adapter connected to an extender sheath connected to a nosecone extension adapter. Such a construction permits the rigid flue to be articulated relative to the articulated joint to center the tip intermediate therein in a rigid yet leak-proof manner. The flexible flue includes a plurality of spaced interior ribs in a similar construction extending in the interior of the body thereof. The connecting end of the flexible flue defines a diameter greater than the diameter of the flexible flue near its connecting end and angularly merging with the flue body.

The nosecone extension defines an articulating joint at one end thereof as having a recess for receiving an O-ring seal at said joint. The nosecone extension is defined by a body defining a passage therein through which passage the ultrasonically-vibrated tip passes. The passage includes an inwardly turned radius at one end thereof for securing the nosecone extension to the nosecone with a snapping action, while permitting rotation of the nosecone extension about the nosecone. The nosecone extension further defines an irrigation fluid passage merging with the tip passage in the nosecone toward its forward end and emerging as an irrigation cowl from the body of the nosecone extension near its inlet end for receiving therein an irrigation fitting for easy connection to irrigation tubing. Such a nosecone extension structure facilitates ready and easy connection of a flue (whether flexible or rigid) with an O-ring seal at the forward end thereof for articulation relative to the protruding tip through the nosecone extension, easy rotatable mating connection with a mating structure on the nosecone, and an irrigation connecting port for ready connection of the irrigation tubing with an irrigation fitting. Preferably, the nosecone extension or transition piece snaps onto the nosecone while allowing rotation of the irrigation port relative to the resonator of the handpiece for convenience of installation.

The irrigation fitting according to the invention comprises a tapered length of tubing defining a first portion angularly bent relative to the remaining portion, a central radially-extending rib for limiting insertion of the tapered end into the irrigation port on the nosecone extension and a barbed exterior end over which irrigation tubing may be securely slip fit while resisting withdrawal therefrom. Such a fitting easily cooperates with the irrigation port on the nosecone irrigation cowl to facilitate connection and location of the irrigation tubing.

According to another aspect of the invention, for use in an assembly of a tip/nosecone/handle subassembly secured at its foward end to an extender for housing an extended tip, a nosecone extension adapter, which is shaped similarly to the nosecone extension previously described, is provided having a rotating joint for connection to the nosecone and a forwardly extending member having an outwardly turned forwardmost portion for securing thereon an extender sheath. In this combination, a flue adapter defining at its forward end an articulating joint and at its aft end a tube and seal arrangement receives either the rigid flue or the ribbed flexible flue as previously described.

In another aspect of the invention, an aspiration tubulation connector is provided for quickly connecting the aspiration tubing securely at one end thereof to an inward port and is connected at its outward port to the aspiration port on the cutting tip through a rotating movement through a slot in the nosecone subassembly. The axis of connection of the aspiration tubing after the tubulation connector is secured lies parallel to the axis of connection of the outward port so that the tubulation connector defines a portion lying on the surface at the exterior of the nosecone and a portion fitted into the slot in the nosecone. This fitting in addition provides a non collapsable key for aspiration connection.

In still another aspect of the invention, the aspiration tubing is connected to a T-valve assembly at a location intermediate the handpiece and a pinch valve and vacuum cannister for connection with a duckbill valve vent fitting.

These and other features of the components of the assembly and of the assembly itself will become further apparent from the detailed written description of the invention which follow, taken in conjunction with the drawings.

BRIEF DESCRIPTION OF THE DRAWINGS

In the drawings:

FIG. 24 illustrates a plan view of the aspiration tubulation connector according to the invention;

FIG. 25, comprising FIGS. 25A, 25B, 25C, 25D and 25E together, illustrates the left side portion of the aspirator tubulation connector respectively showing a plan view, a left end view, a right end view, a top view, and a bottom view of the left side of the aspirator tubulation connector;

FIG. 27, comprising FIGS. 27A, 27B, 27C, 27D, and 27E together, respectively illustrates the right side of the aspirator tubular connector and respectively shows a plan view, a left side view, a right side view, a top view, and a bottom view.

DETAILED DESCRIPTION OF THE PREFERRED EMBODIMENT

Figure 1:
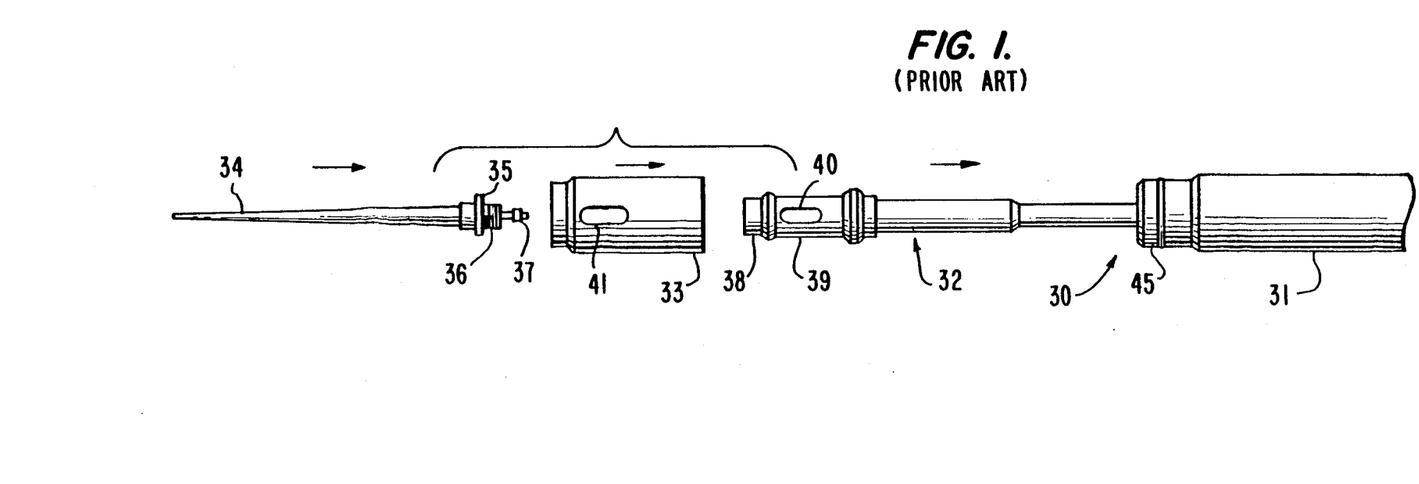
FIG. 1 is a diagrammatic assembly drawing of the handpiece components of a known ultrasonic surgical aspiration system.

FIG. 1 illustrates components of a handpiece of a known ultrasonic surgical aspirator system designated generally by the reference numeral 30. The system 30 includes a handle assembly 31 connected to an ultrasonic transducer and vibrator 32, a nosecone 33 and an ultrasonically-vibrated surgical tip 34. The combination of the vibrator 32 and the tip 34 comprises an accoustic vibrator assembly for vibrating the tip for surgical excision at a frequency in the ultrasonic range. The tip 34 defines an acoustic coupling surface 35 forward of threaded connection 36 and terminates at its aft end in an aspiration port 37, in a manner known to the art. The vibrator 32 defines an internally threaded female threaded portion 38 for mating with the threaded portion 36 of the tip 34. When so threadedly engaged, the aspiration port 37 is lcoated within a chamber 39 defined in the vibrator 32 which is accessed through a slot 40. The nosecone 33 also defines a slot 41 which when threaded to the handle assembly lies in axial alignment and in register with the slot 40. The nosecone 33 is threaded onto an external threads 45 on a threaded portion of the handle assembly 31. Such assemblies are known to the art for their intended purpose.

The procedure for connecting the irrigation and aspiration tubing lines to the assembly 30 in FIG. 1 has been described generally in the Background of the Invention. It should be understood that when the components are fully assembled, the tip 34 defines an annular space at the outlet of the vibrator 32 through the nosecone 33 for conducting irrigation fluid from a fluid source to the surgical site at the distal portion of the tip 34. In addition, aspiration tubing is connected to the aspiration port 37 through the aligned slots 41 and 40 as previously described. It should be further understood that power is supplied to the unit from a console which otherwise controls the parameters of the surgery, including vacuum at a suction port at the face of the unit for controlling the aspiration rate through the aspiration tubing. The irrigation tubing is connected to a source of irrigation fluid located at a predetermined height relative to the surgical site and the manner of use of such instrument in a number of surgical procedures using a console of the type generally described is well-known in the art. Accordingly, the aspects of this invention which relate to its mechanical connections among the various component parts and of the several pieces of tubing forming the completed unit can be abbreviated.

Figure 2:
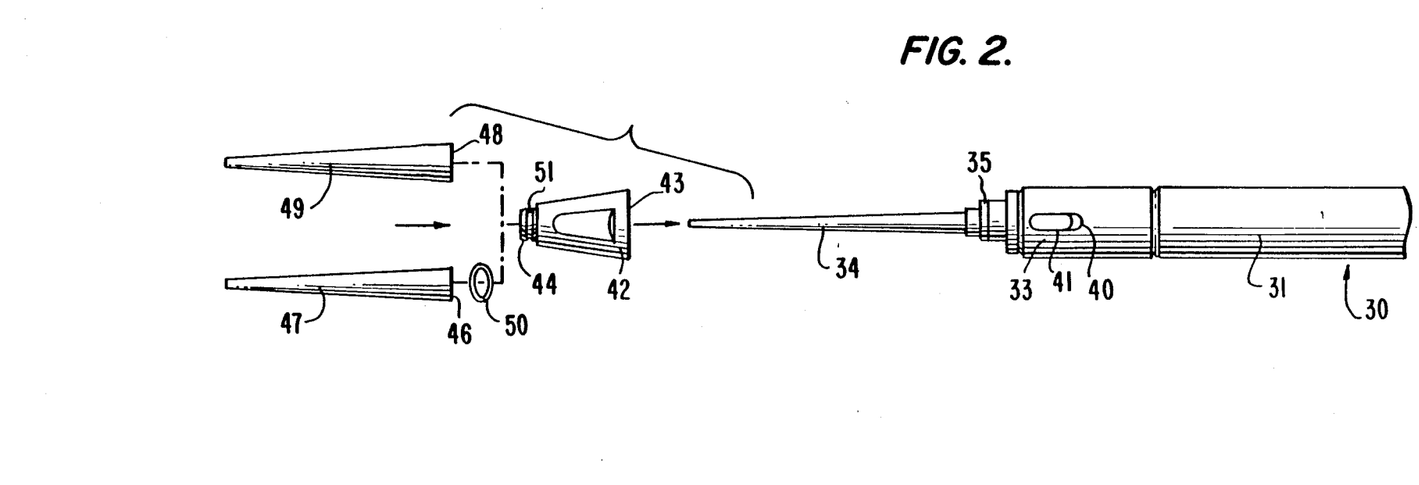
FIG. 2 is an assembly diagram similar to FIG. 1 modified according to the invention to include a nosecone extension with an irrigation cowl adapted for an articulating connection with either a rigid flue or a ribbed flexible flue and a rotating connection to the nosecone.

FIG. 2 illustrates the assembly 30 of FIG. 1 in its assembled state. A nosecone 33 is shown in greater detail in FIG. 6 to provide a basis for understanding the connection of a nosecone extension 42 according to the invention. Throughout this specification the inward, inboard, or inlet side of a component refers to the portion of the component nearer to the handpiece assembly 30, whereas the outward, outboard, or outlet side of the component refers to the side nearer the surgical site and operative tip 34.

Figure 7:
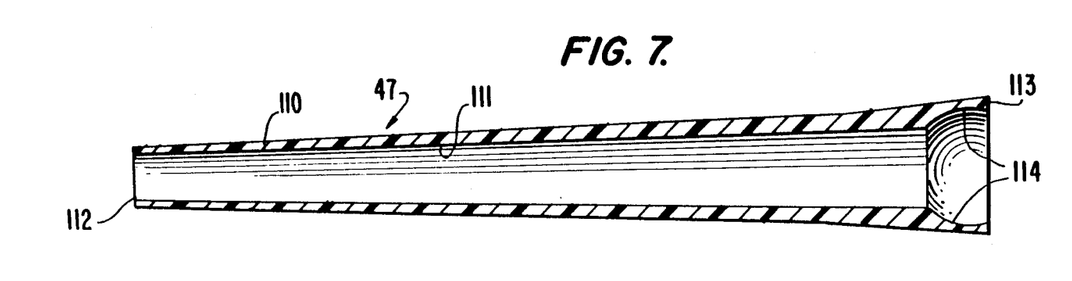
FIG. 7 is a side cross-sectional view of an articulated rigid flue to provide an articulating connection to the articulating joint on the nosecone extension or the flue adapter according to the invention.

Thus in summary, the nosecone extension 42 provides at its inward side a rotating joint 43 which permits the nosecone extension 42 to be snapped on to the nosecone 33 as will be described in greater detail. The extension 42 also defines an outward articulating joint 44 for receiving either a rigid flue 47, shown in FIG. 7, or a flexible flue 49, shown and described in connection with FIGS. 8–10. The articulating joint 44 permits easy insertion of either flue embodiment in an articulated fashion to permit adjustment of the tip centrally of the bore of either flue, and with a leakproof arrangement. Accordingly, the articulating joint 44 may be connected to the inward end 46 of the rigid flue 47 or the inward end 48 of the ribbed flexible flue 49. When te rigid flue 47 is used, an O-ring 50 is mounted in an O-ring recess 51 in the articulating joint 44 to provide a seal to prevent leakage at that connection.

Figure 3:
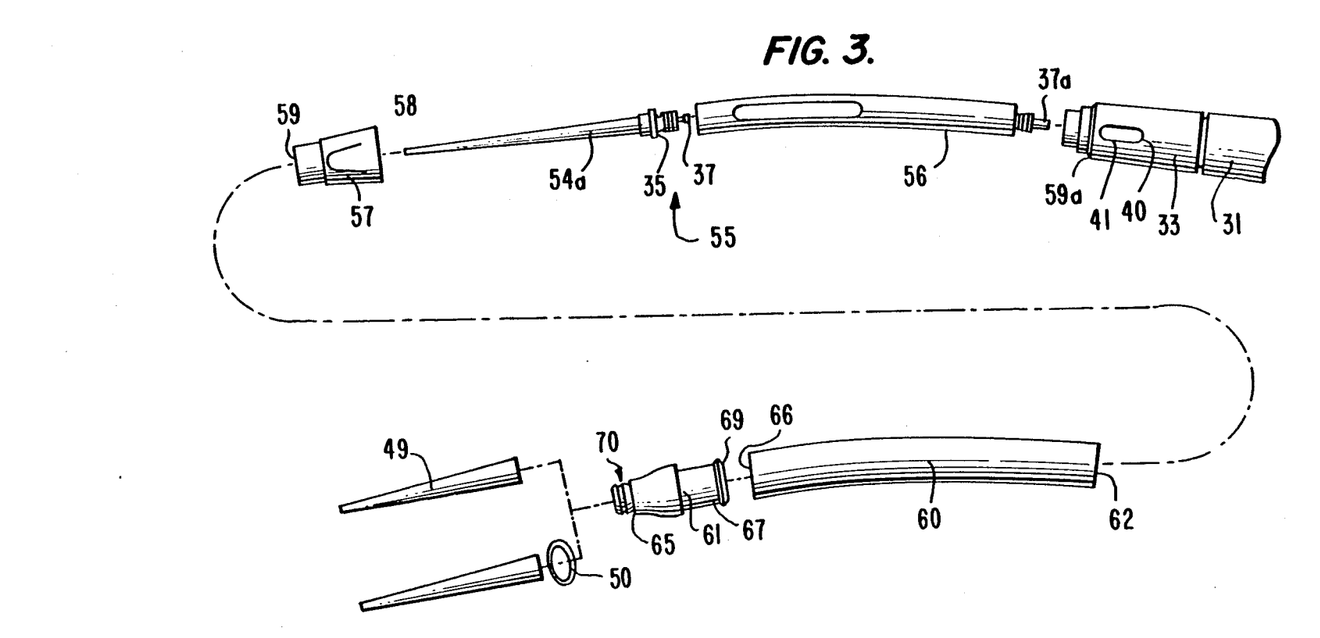
FIG. 3 is a diagrammatic assembly drawing of the components of a modified ultrasonic system using an extender with an extender sheath and extender tip, and illustrating a nosecone extension adapter and flue adapter according to the invention, the former defining an irrigation cowl and a rotating connector with the nosecone, the latter articulatingly connecting either a ribbed flexible flue or a rigid flue.

The development of convenient alternative components has produced the representative alternative embodiment shown in the assembly designated generally by the reference numeral 55 in FIG. 3. That assembly uses an extended tip 54a which is curved as in an extender 56 which together are connected to the handpiece assembly 30 generally in the manner described. A nosecone extension adapter 57 is shown in greater detail in FIGS. 16 and 17 to define at its inward end a rotating joint 58 to be secured to a snap ring assembly 59a on the outboard or outward end of the nosecone 33 in the handpiece assembly 30. The outward end 59 of the nosecone extension adapter 57 is structurally sized and adapted to receive an inward end 62 of a curved extender sheath 60 in a slip fit arrangement thereon. A flue adapter 61, shown in greater detail in FIGS. 18-21, defines at its inward end 68 a cylindrical member 67 having an outwardly flared portion 69 for securing the flue adapter 61 within the wall at the outward end 66 of the extender sheath 60. The outward end 70 of the flue adapter 61 defines an articulating joint 70 similar to the articulating joint 44 on the nosecone extension 42 in FIG. 2 for receiving a ribbed flexible flue 49 or a rigid flue 47 in the same manner as referred to above. The ribbed flexible flue 49 may be conveniently used instead of the rigid flue 47 for curved members such as the tip 54A and the extender 56.

Figure 4A:
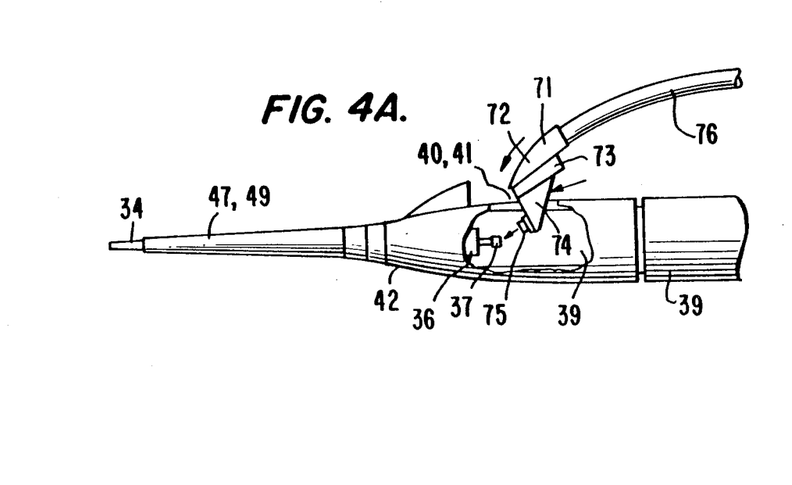
FIGS. 4A and 4B together show the use of an aspirator tubulation connector according to the invention for quickly connecting aspiration tubing to an aspiration port within the nosecone through minimum rotation.
Figure 4B:
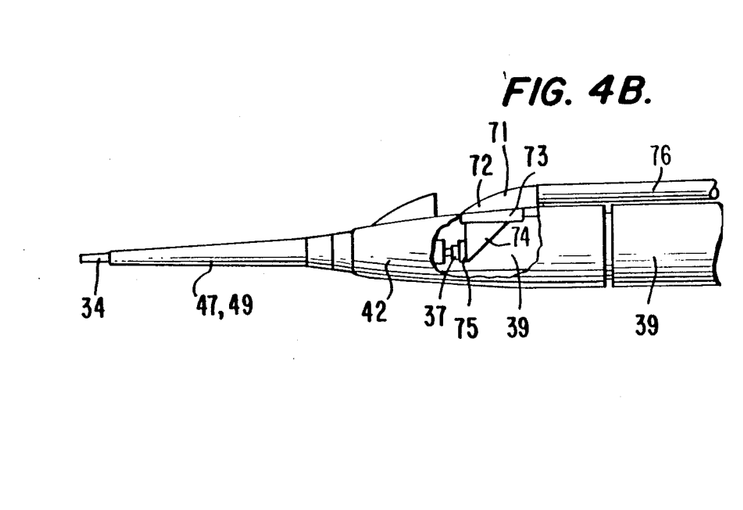
Figures 24, 25B:
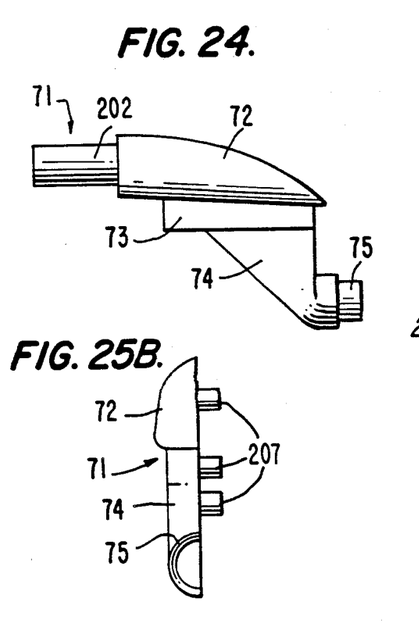
Figures 25A, 25C:
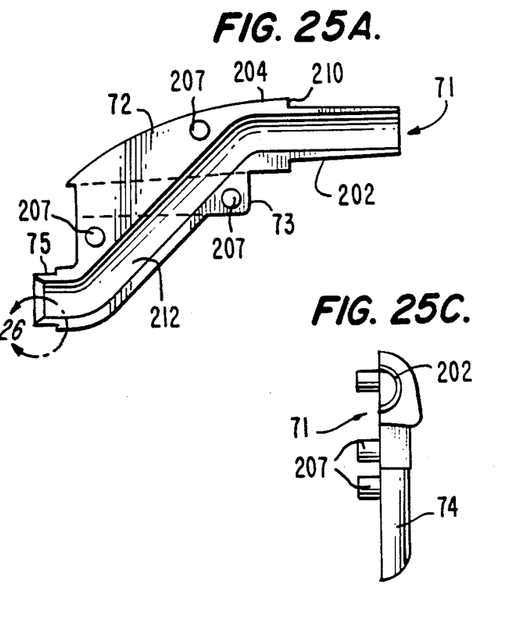
Figure 25D:
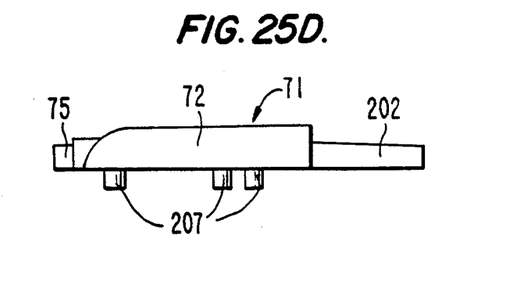
Figure 25E:
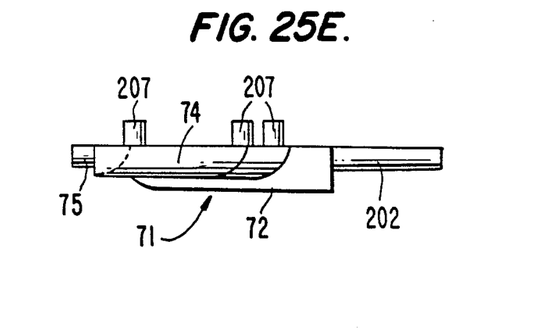
Figure 26:
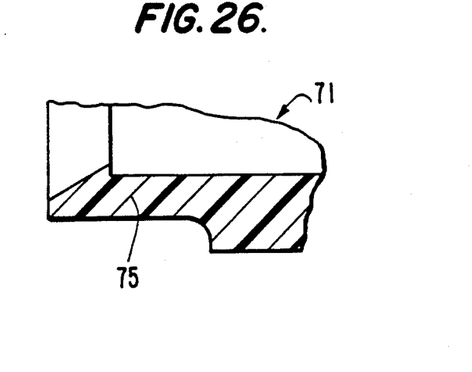
FIG. 26 is a view taken along detail 26 of FIG. 25 showing seal detail.
Figure 27A:
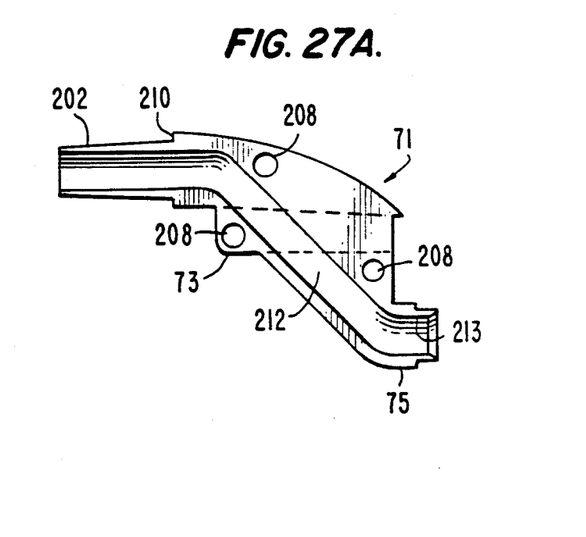
Figure 27B:
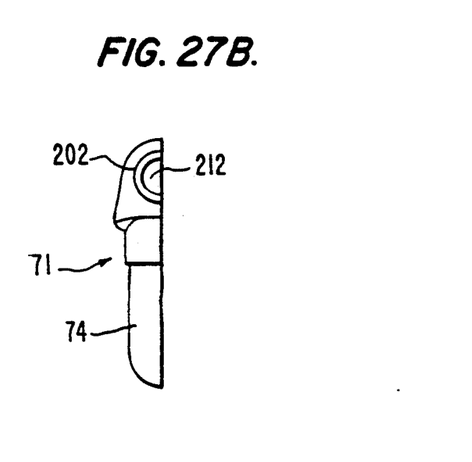
Figure 27C:
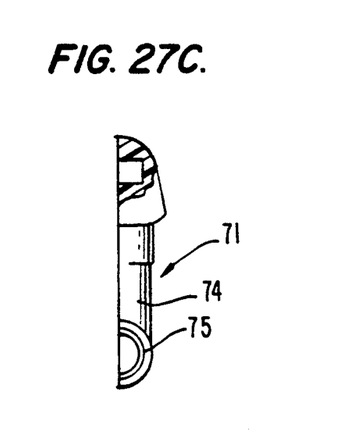
Figure 27D:
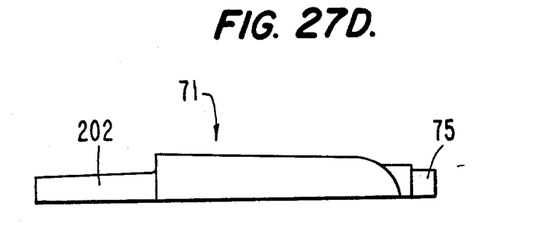
Figure 27E:
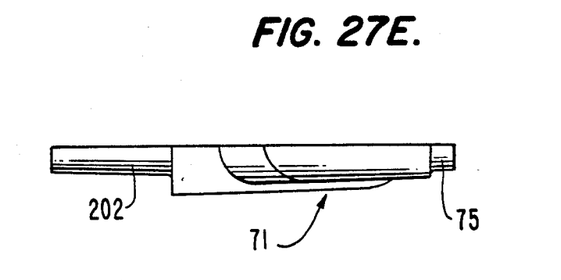

An important feature of the invention, as best seen in FIGS. 4A and 4B and in detail in FIGS. 24–26, involves the use of an aspiration tubulation connector 71 for connecting the aspiration tubing 76 to the aspiration port 37 on the tip 34 within the chamber 39 on the interior of the assembly 30. With the orientation shown in FIG. 4A, the slots 40, 41 lie in the upper portion of the sketches to show the aspiration tubulation connector 71 which has an outer body portion 72 rigidly secured to the aspiration tubing 76 and a transition portion 74 defining an outward port 75 inserted in the slots 40, 41 ready for mating of the outward port 75 with the port 37 of the tip 34. FIG. 4B shows the positioning of the aspirator tubulation connector 71 after the connection is manually made wherein the outer body portion 72 lies along the wall of the nosecone extension 42 and includes a seating portion 73 seated in the slots 40, 41. The body portion 72 is shaped to receive the fingers of the assembler in a convenient fashion, while the seating portion 73 is sized to provide a tactile indication that the outward port 75 has properly engaged the port 37. The details of the aspiration tubulation connector 71 will be described and seen later in connection with FIGS. 24–27. Accordingly, the use of the aspiration tubulation connector 71 according to the invention provides a quick, convenient and fool-proof method for connecting the aspiration tube 76 to the aspiration port 37 and avoids the manipulative difficulty associated with the threading of a cable connected to the aspiration tubing through the aspiration port in the tip after insertion through the slot 41 as in the prior art embodiment. Thus, the connector 71 defines an aspiration passage through the wall of the handpiece assembly 31.

Figures 5, 6:
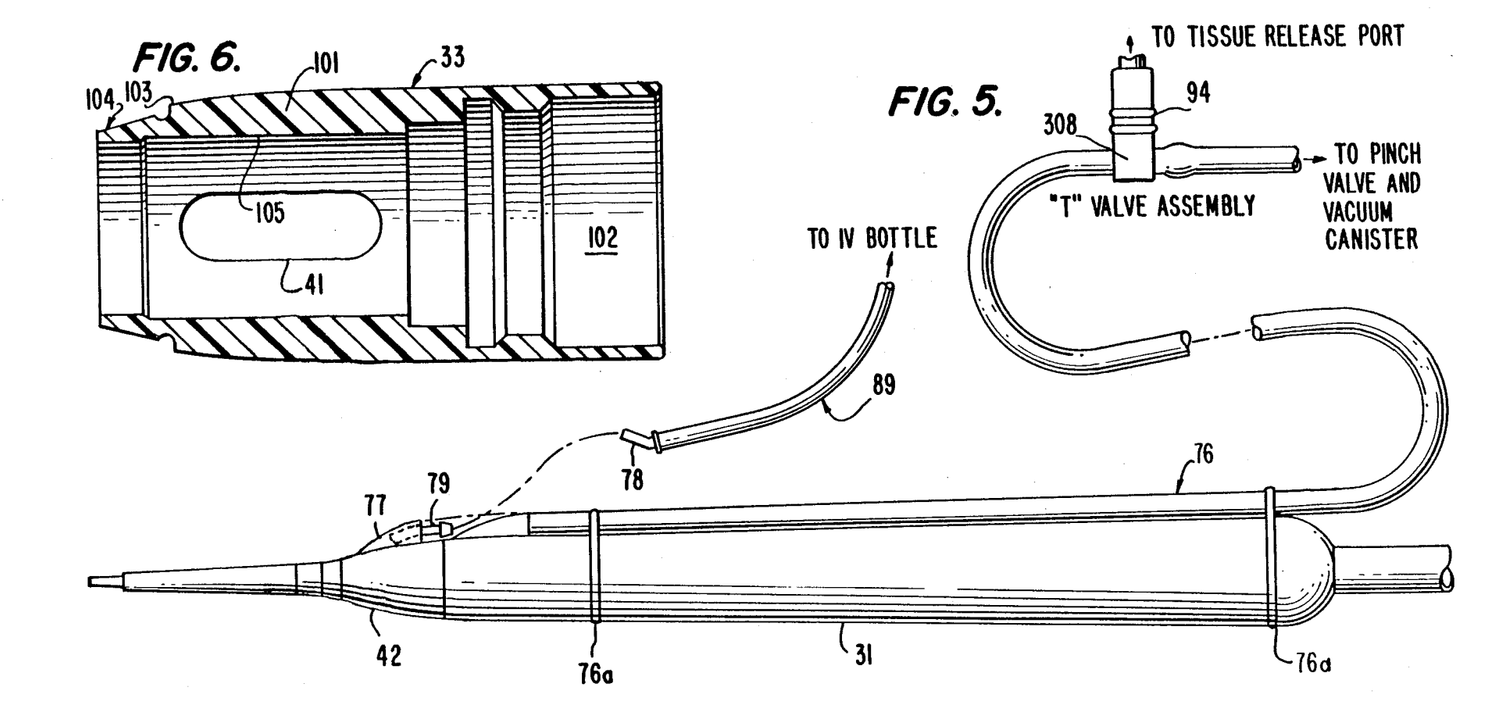
FIG. 5 illustrates the assembled handpiece having the components shown in FIG. 2 and illustrating the improved connectors for the aspiration tube, the irrigation tube, and to the tissue release port on a panel of a control instrument.
FIG. 6 is a side cross-sectional view of a nosecone used in the assemblies of FIGS. 1-5 to which either a nosecone extension or nosecone extension adapter according to the invention is connected.

As shown in FIGS. 4A and 5, after connecting the connector 71 as described, the aspiration tube 76 lies along the body of the handle assembly 31 and is secured thereon by resilient bands 76A similar to the current manner. Because of the rigid or elastomeric structural connection, a fluid tight connection is assured in spite of manipulations of the handpiece during the surgical procedure.

As also shown in general in FIG. 5, the nosecone extension 42 includes an outwardly extending irrigation cowl or housing 77 for receiving an irrigation fitting 78, described in greater detail in connection with FIGS. 22 and 23. An irrigation fitting 78 is inserted in the irrigation housing 77 on the nosecone extension or transition 42 which, upon a certain turn and lock arrangement, secures an irrigation tube 89 to the assembled handpiece 31. The other end of the irrigation tube 89 is connected, as is known, to a hanging bottle of irrigation solution.

FIG. 5 shows a further feature of the assembly according to the invention involving the use of a seal 94 connected to the aspiration tube 76 having therein a duckbill valve connected to a tissue release port on the front panel of a control unit (not shown). Thus, a simple T-valve assembly with seal is defined while the other end of the aspiration tube 76 is connected to a pinch valve on the control console for controlling aspiration, and to a vacuum canister (not shown) for receiving the discharged aspirated particles.

The assembly of components as described in connection with FIGS. 1 through 5 makes simple the connections necessary at the surgical handpiece 31 and elsewhere to brind irrigation to and aspiration from the surgical site. Those components and their assembly avoid the use of plain tubing ends which required skilled special application techniques as described, for making the connections, while providing quick connect devices which allow easy, rapid and fool-proof connection of the irrigation, aspiration, and tissue release ports during setup of the instrument for surgery. The improved transition piece, or nosecone extension 42 on the handpiece 31 further permits an easy exchange of flues between the rigid and flexible embodiments, as may be necessitated or desired during surgery and their articulation for the convenience of the surgeon and to assure smooth even flow of irrigation fluid together withh a swivel joint which permits the use of curved ultrasonic tips, whether of normal length or extended length.

In order to provide the basis for understanding in greater detail the assembly according to FIGS. 2-5, a cross-section of the nosecone 33 is shown in FIG. 6. The nosecone 33 defines a generally cylindrical wall-portion 101 having a circular cross-section defining a plurality of stepped chambers 102 on the inward side thereof and terminating in a snap-ring recess 103 which merges into a tapered forward portion 104 at the forward end thereof. The slot 41 in the nosecone 33 is defined in the wall 101 in the forwardmost portion of the nosecone 33. A chamber 105 is defined interiorly of the slot 41, while one of the stepped chambers 102 defines an interior thread for threaded engagement with mating threads 45 on the handle assembly 31. Preferably, a pair of opposed slots 41 is provided.

The tapered forward end 104 and the recess 103 are sized and arranged to receive conveniently and securely the rotating joint 43 on the nosecone extension 42, as described in connection with FIG. 2.

At the outward end of the nosecone extension 42, either of a pair of flue embodiments 47 and 49 located to define the irrigation fluid passage. Thus, in FIG. 7, a rigid articulated flue 47 is shown in cross-section as defined by an elongated, tapered member 110, preferably made from plastic, and defining an axially elongated bore 111 therein. At its outermost end 112, the bore 111 defines a cross-sectional area sufficient to permit the distal end of the tip 34 to pass therethrough, while defining an annulus between the tip end and the wall 112 for the passage of irrigation fluid therethrough to the surgical site. Preferably, the taper of the interior wall is on te order of about three degrees while the taper of the exterior wall is on the order of about four degrees so that the wall gradually thickens towards its inward end 113. On the interior portions of the inward end 113 are defined a pair of arcuate recesses 114 forming portions of the diameter of a circle and sized to be securely but rotationally received on the articulating joint 44 of the nosecone extension 42. The center of the circle defining the surfaces 114 lies outwardly from the handpiece and, within the body of the unit so that the minimum wall thickness lies inwardly from the end 113. Such an overlapped construction permits a snap fit of the articulated flue onto the articulated joint to facilitate the insertion of the flue on the articulated joint 44 and changing flues as may be necessary or desirable during surgery.

Figure 8:
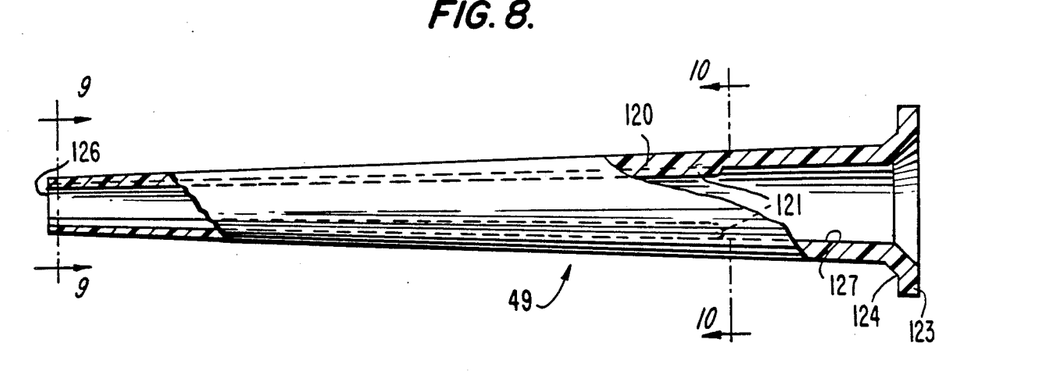
FIG. 8 is a side cross-sectional view of a ribbed flexible connector according to the invention for connection to either the nosecone extension or the flue adapter according to the invention for providing an articulating mounting suitable for curved tip members.
Figure 9:
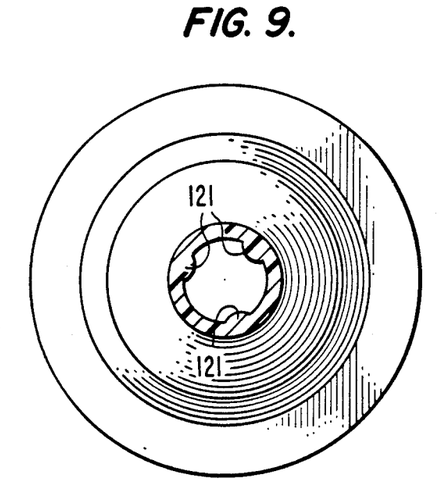
FIG. 9 is a side cross-sectional view taken along line 9—9 of FIG. 8 near the exit port of the flexible flue.
Figure 10:
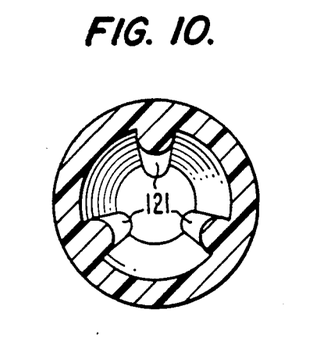
FIG. 10 is a side cross-sectional view taken along line 10—10 of FIG. 8 near the entry port of the flexible flue.

A ribbed flexible flue 49 is shown in FIG. 8 as including an axially elongated body portion 120 generally defined in cross-section with a circular annulus and defining on the interior thereof a plurality of spaced ribs 121 on the interior surface of the body portion 120 along a predetermined length thereof. FIG. 9 illustrates an embodiment in which three such inwardly projecting ribs 121 are used, each located one hundred and twenty degrees apart on the circumference of the bore. At its inward end, the flexible flue 49 is defined by a radially outwardly extending portion 123 which merges into an angular portion 124 which further merges into the wall of the body 120. the ribs provide structural rigidity to the flexible flue 49 while permitting its flexure to accommodate curved tips and to permit easy centering of the flexible flue 49 about the tip 34 located therein, as in the alternative embodiment. A typical taper is on the order of two degrees and the angled portion 124 may be oriented relative to the radially outwardly extending portion 123 at an angle of about forty-five degrees. In the alternative, only a single rib, which is preferably a spiral, may be used, or more than three ribs, such as six ribs located sixty degrees apart, may be used. FIG. 9 illustrates a cross-section of the flexible flue 49 taken near its outward end 126, while FIG. 10 shows a cross-section taken at about the location in the interior of the flexible flue 49 where the ribs 20 terminate so that the portion 127 is free from such interior ribs.

FIGS. 11-15 together illustrate the nosecone extension 42 shown in the embodiment of FIG. 2. As described, the nosecone extension 42 is characterized as providing a rotating joint 43 at its inward or rearward end, and an articulating joint 44 at its outward or forward end. The nosecone extension 42 is defined by a body 140 which includes a generally cylindrically portion 141 and an integral tapered conical portion 142 which tapers to its maximum diameter at its inboard end 143. The nosecone extension is preferably made from a suitable medical grade plastic such as polycarbonate. The area in which the tapered portion 142 merges into the generally cylindrically portion 141 is defined by a gentle recess 143. Outwardly of the portion 141 is formed a generally circular cross-sectioned articulating joint having a recess 146 between circular areas. The outward surfaces of the arcuate portions 144 and 145 of the articulating joint 44 lie on the diameter of a circle having its center on the axis of the nosecone extension 42. The diameter of the circle is sized to receive the inward end of either the ribbed flexible flue 49 or the rigid flue 47 in a snap fit, quick-connect relationship which is secure and leakproof.

Figure 13:
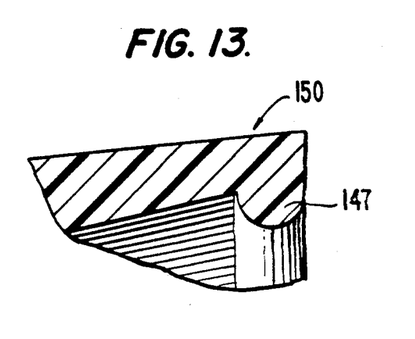
FIG. 13 is a cross-sectional view of Detail 13 taken as shown in FIG. 12.

At the inward end of the nosecone extension 42 as defined by the wall 143, a radially-inwardly projecting seal 147 is provided in the form of a bead or rim which is semi-circular in cross section as shown in enlarged detail in FIG. 13. The bead or rim 147 acts as a camming and locking member when the nosecone extension 42 is inserted onto the nosecone 33 so that the bead 147 rests in the recess 103 after camming along the surface 104 of the nosecone 33, as shown in FIG. 6.

Figure 11:
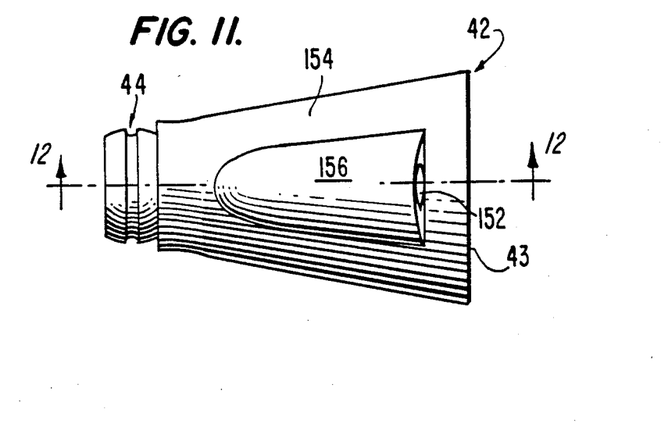
FIG. 11 is a side plan view of a nosecone extension used in the embodiment of FIG. 2 to connect either flue embodiment to the nosecone.
Figure 12:
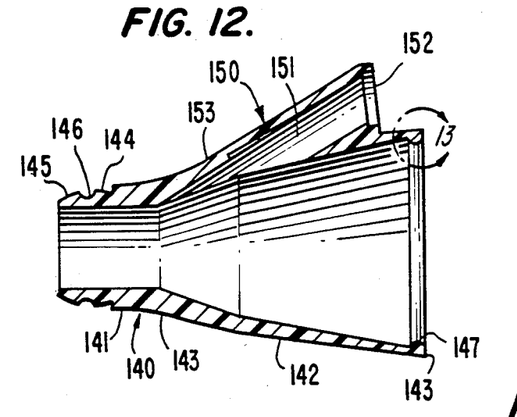
FIG. 12 is a cross-sectional view taken along line 12—12 of FIG. 11 and rotated through ninety degrees to illustrate the irrigation cowl and tubing port for receiving the irrigation tubulation connector.
Figure 14:
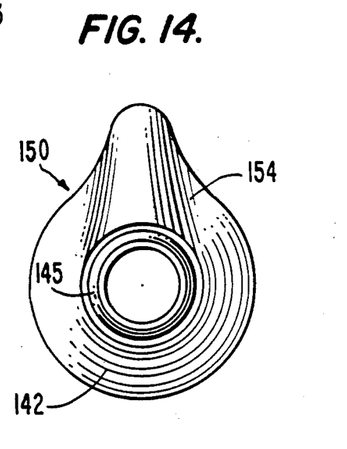
FIG. 14 is an end view taken from the exit end of FIG. 12 showing the articulating joint of the nosecone extension according to the invention.
Figure 15:
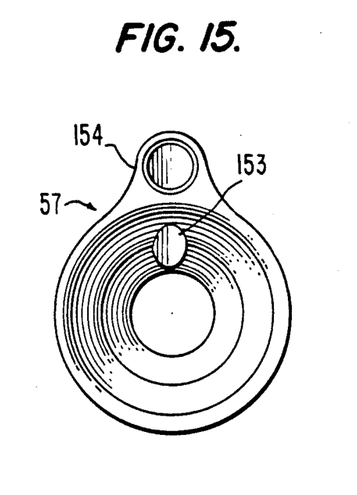
FIG. 15 is an end view taken from the end of the nosecone extension opposite to that shown in FIG. 14 and further illustrating entry of the irrigation port into the tip passage defined by the nosecone extension according to the invention.

An irrigation cowl is generally depicted by the reference numeral 150 and defines an irrigation opening through an angled bore 151 therein terminating in an inlet irrigation port 152. The center line of the generally cylindrical irrigation bore 151, for the passage of irrigation fluid into the nosecone extension 42, lies at an angle relative to the axis of the nosecone extension 42 so that the bore 151 defines an elliptical opening 153 in the outwardly descending-diameter interior bore of the wall portion 142, as best seeen in the side view of FIG. 15. The irrigation cowl 150 includes a wall body portion 153 having an irregular contour 154 as shown in FIGS. 11, 13 and 14 to merge attractively with the nosecone extension 42. Such a nosecone extension 42 is convenient as providing a quick connection to the nosecone 33 itself at its inlet end by a mere snap fit coaction wherein the bead 147 cams on the outward surface of the nosecone 33 and snap fits into the recess 103 of the nosecone 33 with a tactile indication which may also be heard by the assembler. In addition, such an arrangement permits rotation of the nosecone extension 42 about the nosecone 33 to orient the irrigation cowl 150 and hence the irrigation inlet opening 152 to a convenient circumferential location for connection of the irrigation tube 89 (see FIG. 5).

Similarly, the outlet end of te nosecone extension 42 provides a convenient quick connection for a flue 47, 49 which not only permits articulation of the flue to orient the outlet of the flue in a particular direction relative to the axis of the nosecone, but also to center the flue around the tip therein, thus to accommodate tips of alternate shapes. The cooperating structure between the inlet of the flue and the outlet of the nosecone permits rotation of the flue thereabout and a tactile indication that the flue is properly seated upon the outlet of the nosecone extension.

Figure 16:
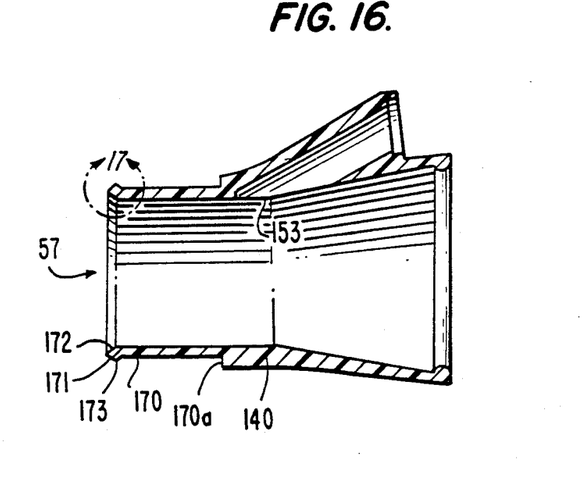
FIG. 16 is a side cross-sectional view of a nosecone extension adapter having a rotating connecting end for use in the embodiment of FIG. 3 for connecting an extender sheath at its outboard port and connection to the nosecone at ist inboard port in the embodiment of FIG. 3 using tip and curved extender with an extender sheath.
Figure 17:
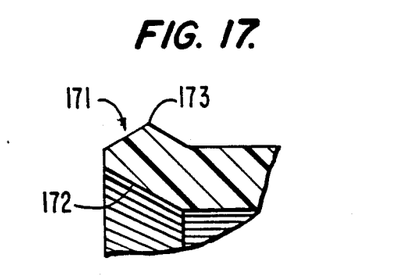
FIG. 17 is a cross-sectional view of Detail 17 taken as shown in FIG. 11 at the outboard port of the nosecone extension adapter according to the invention.

FIGS. 16 and 17 illustrate a nosecone extension adapter 57 for use with an extender sheath 60 when a curved elongated tip 54a and associated extender 56 are used, as shown in FIG. 3. With respect to the inlet end of the nosecone adapter 57, its components are similar to the inlet components of the nosecone extension 42 described in connection with FIGS. 12-15. Thus, like reference numerals are utilized. Its outlet end differs, however, to provide a quick connection to an extender sheath 60. Thus, the portion 140 merges into a second cylindrical portion 170 defined in cross section by an annulus and extending outwardly from the wall portion 140 to define at its outermost suface an outwardly-flared portion 171, shown in detail in FIG. 17. The inside diameter of the outwardly-flared portion 171 is defined by an outwardly tapering surface 172 while the outside diameter of the flared portion terminates in an apex 173 having a relative maximum diameter. The structure thus permits an extender sheath 60 to be slip fit over the outward end of the nosecone extension adapter 57. and secured therein in a slip fit relation to an extent limited by the shoulder 170a. The apex 173 provides resistance to withdrawal of the extender sheath from the nosecone extension adapter 57 while the tapered portion 171 permits a camming action of the extender sheath thereon during the insertion process to facilitate assembly. Otherwise, the elements of the nosecone extension adapter 57 are like those shown for the nosecone extension 42 ad cooperate in the same manner.

The articulating joint which was omitted from the nosecone extension adapter 57 is included on the outlet of the flue adapter 67 shown in FIGS. 18-21. Thus, the flue extender adapter is structured to be inserted into an end of the extender sheath 60 opposite to that which receives the outlet end of the nosecone extension adapter. The articulating joint 70 of the flue adapter 67 is structured like the articulating joint on the nosecone extension 42 and thus need not be described in greater detail. The flue adapter 67 is defined by a body portion 180 having an inlet cylindrical portion 181 defining at its inlet end 182 an apex 183 structured similarly to the outlet configuration of the nosecone extension 57. Thus, like reference numerals are used.

Figure 18:
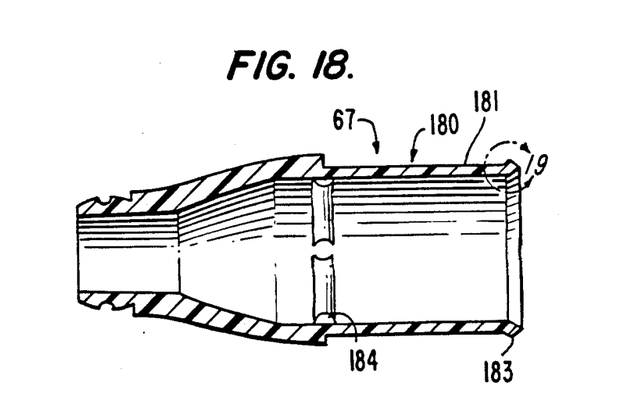
FIG. 18 is a side cross-sectional view of a flue adapter for use in the embodiment of FIG. 3 for connection at its inboard port to the extender sheath and having an articulating joint at its outboard port for connection to either flue embodiment.
Figure 19:
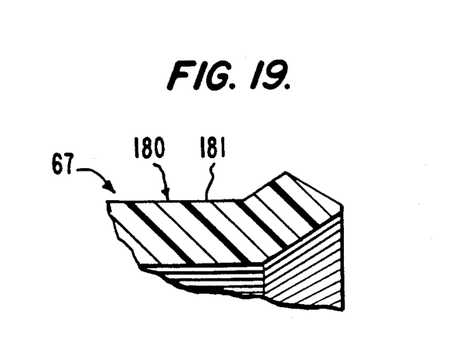
FIG. 19 is a cross-sectional view of Detail 19 shown in FIG. 18.
Figure 20:
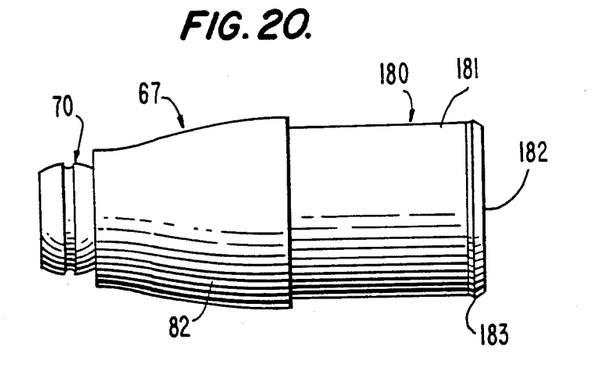
FIG. 20 is a plan view of the flue adapter according to the invention from which the cross-section of FIG. 18 is taken.
Figure 21:
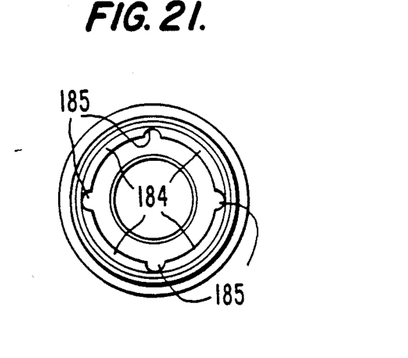
FIG. 21 is an end view of the flue adapter shown in FIGS. 18-20 showing its internal centering rib.

The cylindrical portion 181 merges into a thickened outward wall portion 82 which tapers downwardly toward the outlet end of the flue adapter 67 to define the articulating joint 70. At the area of merger between the thickened wall portion 182 and the cylindrical wall portion 181, a radially inwardly directed wall portion 184 is included, as best seen in cross section in FIG. 21. The interiorly-directed wall portion 184 thus defines a plurality of spaced semi-circular portions 185 equally spaced about the circumference of that wall portion to provide water passage through the structure. Preferably, the flue adapter is made from a suitable medical grade plastic such as polycarbonate.

Figure 22:
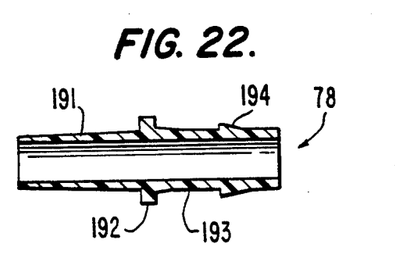
FIG. 22 is a side cross-sectional view of the construction of the irrigation fitting shown in FIG. 5 for insertion into the nosecone extension of FIGS. 11-15 on the nosecone extension adapter of FIG. 16.
Figure 23:
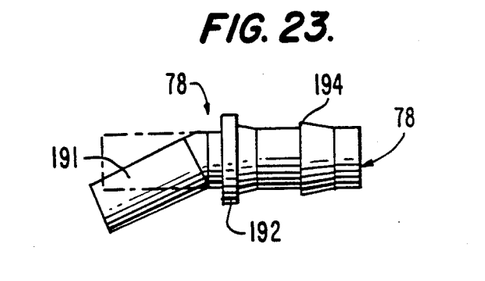
FIG. 23 is a side plan view of the irrigation fitting showing its contour and bend after turning when in place.

Returning to the embodiment of FIGS. 2, 3, and 5, an irrigation fitting 78, shown in FIGS. 22 and 23, is utilized. The irrigation fitting 78 has an outlet end which is slip fit into the irrigation port on either the adapter or on the nosecone extension 42 and has its inlet end suitably structured for receiving thin-walled tubing thereon. FIG. 22 thus shows a cross section of the irrigation fitting 78 having a tapered outlet wall portion 191, a central upwardly raised portion 192 terminating in an inlet wall portion 193 having a radially outwardly extending barb 194 for securing the irrigation tubing 89 thereon. The taper of the outlet wall portion 191 facilitates its insertion into the irrigation port 79, while the barb 194 resists withdrawal of the irrigation tubing 89 from the fitting 78. The central upraised wall portion 192 provides a suitable bi-directional barrier against overinsertion of the irrigation fitting 78 into the irrigation port 79 and a suitable stop for the end of the irrigation tubing 89 when assembled as indicated diagrammatically in FIG. 4. In practice the fitting has its outlet end 191 cold bent as seen in FIG. 23 after turning to a suitable angle, such as about twenty four-degrees, so that the fitting 190 can be inserted into the irrigation tube 89 and thus inserted into the irrigation port having a correct angular orientation to direct the irrigation tube outwardly and parallel relative to the body of the nosecone extension to the outside of the aspiration tubulation connector, as well as parallel to the body of the handpiece 31. The irrigation tubing may also be secured by clips.

The aspiration tubulation connector 71 is shown in contour in FIG. 24 as defining an outward port 75 for mating with the aspiration port 37 on the tip 34 and an inward port 202 for receiving and end of the aspiration tube 76 in a secure relationship. The aspiration tubulation connector 71 further includes a fluid passage between the inward port 202 and the outward port 75 through the exterior body portion 72, the fitting portion 73 and the transition portion 74. As can be seen from FIGS. 3 and 4, when the aspiration tubulation connector 71 is snap fit into place within the nosecone extension, its snap fit portion 73 is rigidly secured within the slot 40, 41 defined in the nosecone 33. Similarly, its outwardly extending body portion 72 lies along the outside wall of te handpiece so that its inward port 202 is axially directed to accomodate the aspiration tube 76 along the exterior of the handpiece as shown in FIG. 4.

Preferably, the aspiration tubulation connector 71 is made of a left side component shown in FIGS. 25A through 25F and a mating right side component as shown inFIGS. 27A through 27F. The left side portion and the right side portion are thus joined together by matting male members 207 in the left side component with female openings 208 on the right side component. The inward portion 202 is tapered so that the aspiration tubing readily slides thereon to a shoulder 210 defined adjacent the portion 204. The interior passage between the inlet 202 and the outlet 201 is designated generally by the reference numeral 212 and is thus shown in either of FIGS. 25 and 27. The inward port 202 defines an outwardly tapered inlet portion 212 in the outermost wall of the outlet portion 213 to permit easy envelopment of the aspiration port on the tip. Preferably, the aspiration tubulation connector is made from a suitable medical grade material such as polycarbonate. The operation of the tubulation connector has been described in connection with FIGS. 3 and 4 and the connector is structured so as to permit ready and easy connection as described.

Figure 28:
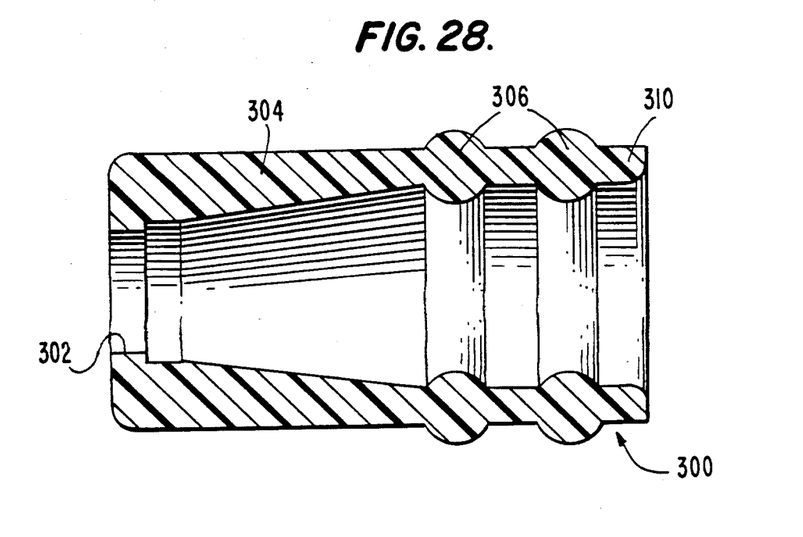
FIG. 28 is a cross-sectional view of the seal used for connection to the vacuum port on the panel of an instrument for controlling one of the system parameters.

FIG. 28 shows a seal 300 in cross-section for providing a quick, positive, uncomplicated connection by a one-way valve (not shown) to a tissue release port on a console, as shown in FIG. 5. The outward end 302 receives a vacuum tubing end in a slip fit relationship. The seal 300 includes a irregularly-shaped wall 304 having a plurality of protrusion 306 for a slip fit connection to a T-valve assembly 308 shown in FIG. 5, by insertion of a tip 310 prior to the T-valve assembly. The protrusion 306 and in manipulating that insertion. The seal 300 thus provides an effective connector for tubing otherwise directly connected to the T-valve assembly 308.

The invention may be embodied in other specific forms without departing from its spirit or essential characteristics. The present embodiments are, therefore, to be considered in all respects as illustrative and not restrictive, the scope of the invention being indicated by the claims rather than by the foregoing description and all changes which come within the meaning and range of the equivalents of the claims are therefore intended to be embraced therein.

What is claimed is:

1. In combination with an ultrasonic surgical aspiration system of the type which includes a handpiece which includes a source of ultrasonic vibrations, a nosecone, and an ultrasonically vibrating tip having a portion connected to said source wherein said nosecone envelops at least a portion of said tip, the improvement comprising:
    an irrigation manifold means for defining an irrigation manifold to provide a passage for irrigation fluid from a source of irrigation fluid to a surgical site adjacent the outward end of said surgical tip,
    said irrigation manifold means including a member rotatingly connected to said nosecone and defining an irrigation passage oblique to an axis of said tip,
    said irrigation passage terminating in an irrigation port structurally adapted for connection to irrigation tubing to provide irrigation fluid to the interior of said member,
    said member defining at its outward port a connection means for quick connection to an end of a flue structurally adapted to envelop a portion of said tip, and
    said flue and said member together defining an irrigation passage for flow of irrigation fluid from the interior of said member communicating with said source of irrigation fluid through said irrigation port and in the space defined by the outside of said tip and the interior of said flue.

2. An ultrasonic surgical system comprising:
    a nosecone having a nosecone forward end and defining a nosecone bore at said forward end,
    a flue attached to said forward end and having a flue bore passing therethrough and communicating with said nosecone bore,
    an ultrasonically-vibrated surgical tip connected at an inward end thereof to said nosecone and pasing through said nosecone and flue bores,
    said surgical tip and said nosecone bore defining a passageway therebetween,
    said nosecone at said forward end having a nosecone outer surface and defining an irrigation port passing through said nosecone outer surface,
    an irrigation cowl attached to and extending out from said nosecone outer surface and over said irrigation port, and disposed generally rearwardly relative to said nosecone,
    an irrigation connector positioned at least partially in said irrigation cowl and providing fluid communication with said passageway,
    an irrigation tube connected to a source of irrigation fluid and having an irrigation tube end, and
    an angled irrigation fitting comprising a first fitting part at said irrigation tube end and a second fitting part angled relative to said first fitting part and connectable to said irrigation connector in an insertion-and-turn arrangement.

3. The system of claim 2 including,
    said irrigation connector extending rearwardly out of said irrigation cowl.

4. The system of claim 3 including,
    said irrigation cowl sloping forwardly and inwardly towards said nosecone outer surface.

5. The system of claim 2 including,
    said nosecone comprising a nosecone member and a nosecone extender attachable to and rotatable relative to said nosecone member, and
    said irrigation cowl and said irrigation port being disposed on said nosecone extender.

6. The system of claim 2 including,
    said irrigation connector including an enlarged outer male member onto which said second fitting part fits.

7. The system of claim 6 including,
    said male member being positioned outside and rearwardly of said irrigation cowl.

* * * * *

UNITED STATES PATENT AND TRADEMARK OFFICE
CERTIFICATE OF CORRECTION

PATENT NO. : 4,846,790

DATED : July 11, 1989

INVENTOR(S) : Robert W. Hornlein, Joseph N. Logan, Alan Broadwin

It is certified that error appears in the above-identified patent and that said Letters Patent is hereby corrected as shown below:

Title page:

Item 75, delete "Vaclav O. Podany, New Fairfield, Conn.".

Item 73, delete "Santa Clara, Calif." and insert
-- Stamford, Conn. --.

Signed and Sealed this

Second Day of October, 1990

Attest:

HARRY F. MANBECK, JR.

*Attesting Officer*      *Commissioner of Patents and Trademarks*